United States Patent [19]
Northrup et al.

[11] Patent Number: 5,882,496
[45] Date of Patent: Mar. 16, 1999

[54] POROUS SILICON STRUCTURES WITH HIGH SURFACE AREA/SPECIFIC PORE SIZE

[75] Inventors: M. Allen Northrup, Berkeley; Conrad M. Yu, Antioch; Norman F. Raley, Danville, all of Calif.

[73] Assignee: The Regents of the University of California, Oakland, Calif.

[21] Appl. No.: 807,152

[22] Filed: Feb. 27, 1997

[51] Int. Cl.$^6$ .......................... G01N 27/27; B01D 24/00; B01D 53/22
[52] U.S. Cl. .................. 204/601; 210/502.1; 210/506; 55/523; 96/11
[58] Field of Search .................. 210/502.1, 506; 96/11 SP, 11; 55/523; 204/601, 605

[56] References Cited

U.S. PATENT DOCUMENTS

| | | | |
|---|---|---|---|
| 4,645,605 | 2/1987 | Durham | 210/502.1 X |
| 5,004,544 | 4/1991 | Hay et al. | 210/490 |
| 5,139,624 | 8/1992 | Searson et al. | 205/656 |

*Primary Examiner*—Donald R. Valentine
*Attorney, Agent, or Firm*—L. E. Carnahan

[57] ABSTRACT

Fabrication and use of porous silicon structures to increase surface area of heated reaction chambers, electrophoresis devices, and thermopneumatic sensor-actuators, chemical preconcentrates, and filtering or control flow devices. In particular, such high surface area or specific pore size porous silicon structures will be useful in significantly augmenting the adsorption, vaporization, desorption, condensation and flow of liquids and gasses in applications that use such processes on a miniature scale. Examples that will benefit from a high surface area, porous silicon structure include sample preconcentrators that are designed to adsorb and subsequently desorb specific chemical species from a sample background; chemical reaction chambers with enhanced surface reaction rates; and sensor-actuator chamber devices with increased pressure for thermopneumatic actuation of integrated membranes. Examples that benefit from specific pore sized porous silicon are chemical/biological filters and thermally-activated flow devices with active or adjacent surfaces such as electrodes or heaters.

23 Claims, 3 Drawing Sheets

POROUS SILICON STRUCTURES WITH HIGH SURFACE AREA/SPECIFIC PORE SIZE

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to porous silicon, particularly to the fabrication and use of porous silicon structures, and more particularly to the fabrication and use of structures which benefit from a high surface area or a specific pore size of porous silicon.

In recent years crystalline silicon micromachining technology has enabled the development of numerous miniaturized devices such as chemical reaction chambers, micro-actuators, micro-grippers, microvalves, etc. Also, it has been recently established that miniaturized porous silicon structures can be fabricated using micromachining technology. P. C. Searson, "Porous Silicon Membranes", Appl. Phys. Lett. 59 (7), 12 Aug. 1991; and S. Ottow et al., "Processing Of Three-Dimensional Microstructures Using Microporous n-Type Silicon", J. Electrochem. Soc., Vol. 143, No. 1, January 1996. Porous silicon is a material that is fabricated from crystalline silicon. Very small pores (nm-$\mu$m diameters) can be introduced with a relatively high degree of uniformity and control. The present invention is based on the recognition that porous silicon compared to crystalline silicon provides a means to significantly increase the surface area of a silicon device or provide specific pore size arrays, while maintaining capability of modifying them with integrated circuit (IC) processes, or by micromachining processes. For example, a doped porous silicon membrane with appropriate pore diameter, which can be fabricated using known IC processes, could be used to provide a resistive heater and/or it could contain electrodes or arrays of electrodes to control the flow of electrically charged chemicals through the pores (such as in electrophoresis). A heated porous silicon membrane could be used to control the viscosity or surface tension of a fluid, thereby making it a selectable/active filtering or valving device. The high surface area of such a porous silicon heater is expected to increase the internal pressure of a liquid/vapor filled closed cavity, thereby increasing the force generated for membrane deflection in a microfabricated thermopneumatic valve. As well, the high surface area pores of porous silicon could be coated with specific coatings for the adsorption/desorption of liquids or gasses, thereby creating a chemical species concentrator. The specific pore size of the porous silicon enables its use as chemical/biological filters and thermally-activated flow devices with active or adjacent surfaces such as electrodes or heaters.

SUMMARY OF THE INVENTION

It is an object of the present invention to provide porous silicon structures.

A further object of the invention is to utilize the high surface area and/or the specific pore size of porous silicon for a variety of applications on a miniature scale.

Another object of the invention is to utilize porous silicon structures to increase surface area of heated reaction chambers and thermopneumatic sensor-actuators, for example.

Another object of the invention is to utilize the high surface area or the specific pore sizes of porous silicon for significantly augmenting the adsorption, vaporization, desorption, condensation, and flow of liquids and gasses in applications that use such processes on a miniature scale.

Another object of the invention is to provide a process whereby porous silicon membranes can be attached to material such as Pyrex.

Other objects and advantages of the present invention will become apparent from the following description and accompanying drawings. The invention involves porous silicon structures and the fabrication of same for high surface area or specific pore size. Porous silicon structures, compared to crystalline silicon structures, provide increased surface area for applications such as chemical reaction chambers with enhanced surface reaction rates, sample preconcentrators designed to adsorb and subsequently desorb specific chemical species from a sample background, or sensor-actuator chamber devices with increased pressure for thermopneumatic actuation of integrated membranes. The porous silicon structures, compared to crystalline silicon structures, provide specific pore size for applications such as chemical/biological filters and thermally/activated flow control devices with active or adjacent surfaces such as electrodes or heaters. By the use of microfabricated porous silicon structures, the state-of-the-art is expanded in the field of chemical reaction systems for synthesis or processing of organic, inorganic, or biochemical reactions. The current micromachining technology for porous silicon expands the use of silicon in preconcentrator structures for analytical instruments, thermopneumatic or thermofluidic valves, as well as filters for biological/chemical sample preparation and cleanup. Very small pores (nm-$\mu$m diameters) can be introduced into crystalline silicon with a relatively high degree of uniformity and control. The porous silicon with appropriate pore diameter, like crystalline silicon, can be processed using conventional integrated circuit and micromachining processing. For example, a porous silicon membrane doped using existing doping techniques can be used to provide a resistive heater and/or it can contain electrodes or arrays of electrodes to control the flow of electrically charged chemicals through the pores, such as in electrophoresis applications. Also, the high surface area pores of porous silicon can be coated with specific materials by existing silicon processing technology for the adsorption/desorption of liquids or gasses. In addition, the porous silicon can be fabricated as thin membranes (~50 $\mu$m thick) which can be bonded to other materials, such as Pyrex or glass, and utilized as an interface element between a PCR and electrophorus devices for DNA integration applications.

BRIEF DESCRIPTION OF THE DRAWINGS

The accompanying drawings, which are incorporated into and form a part of the disclosure, illustrate embodiments of structures using porous silicon membranes in accordance with the invention and, together with the description, serve to explain the principles of the invention.

DETAILED DESCRIPTION OF THE INVENTION

The invention is directed to porous silicon structures having surface area and/or specific pore size, which provides advantages over similar structures of crystalline silicon. Porous silicon provides a means to significantly increase the surface area of a silicon device for use, such as in a heated reaction chamber, and/or provides specific pore size arrays, for use such as in chemical/biological filters, while maintaining the capability of modification, such as being doped or coated using conventional integrated circuit and micromachining techniques.

The following description of the invention is set forth under five (5) categories as follows: 1) porous silicon membrane formation procedure, 2) porous silicon material optimization, 3) small volume adsorption measurement test chamber, 4) controlled flow gas/fluid interface, and 5) PCR/electrophoresis interface.

Porous Silicon Membrane Formation Procedure

Figure 1:
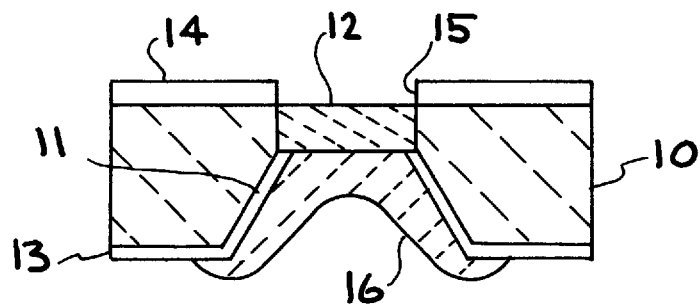
FIG. 1 schematically illustrates porous silicon membrane formation in bulk crystalline silicon.

Porous silicon membrane formulation in bulk crystalline silicon in order to characterize gas or fluid transport of material is shown in FIG. 1. Broadly the formation procedure utilizes pre-etch of a bulk silicon wafer to address large etch rate differential between crystalline and porous silicon, p++ back diffusion to promote full completion of the membrane, and a high integrity nitride backseal to minimize HF solution penetration to the wafer backside metal contact plate. The procedure is applicable to membranes on Pyrex with an additional bulk silicon etchback step and use of an O-ring for porous silicon definition, as described hereinafter. The forming or fabrication process of a device as illustrated in FIG. 1 is carried out by using a bulk crystalline silicon substrate or wafer 10 and forming a tapered opening 11 therein by micromachining or etching to form a bulk membrane of crystalline silicon. Next, a silicon nitride layer 14 is deposited on the opposite side of the tapered opening 11 or polished side of the silicon substrate 10. The silicon substrate 10 is then diffused to form a p++ back diffusion layer 13. An opening 15 is patterned and processed in the layer 14 to expose the silicon membrane region 12. A high integrity nitride backseal 16 is deposited over the opening area adjacent the back diffusion layer 13 to minimize HF solution penetration to the substrate backside metal contact plate, not shown. A porous silicon membrane 12 is formed at the end of tapered opening 11 by electrochemical etching to form small pores in the bulk silicon, described in greater detail hereinafter. Variations in this fabrication process is expected to allow formation of nm to μm size pore diameter material in the membrane region.

One set of electrochemical etch conditions used to form 10 nm diameter pore material was the use of p+ substrates of 0.05 Ω-cm resistivity and 19.2 mA/sq cm current density using 49% hydrogen fluoride (HF) solution. The solution was occasionally stirred to prevent or remove bubbles on the silicon surface exposed to the HF solution. The voltage from the contact plate to the solution was monitored for the time at which its magnitude started to rise significantly; the etch process was terminated at about 2 minutes later.

Porous Silicon Material Optimization

Use of intermediate pore material (~100 nm diameter) compared to small pore material (~10 nm diameter) for optimizing fabrication and device operational requirements, provides easier lithographic definition of array patterns. Pattern alignment to the silicon substrate is also expected to be non-critical compared to conventional approaches. Minimizing of oxide to silicon fiber thickness ratio is beneficial in order to extend temperature limit of material past 600° C. as well as significantly reduce membrane compressive stress and thus increase burst pressure. Provides potential to increase the gas or fluid flow as well as amount absorbed with increased pore conductance. Larger pores are also more conductive to coating the pores with other materials in order to enhance adsorption of the surface. Surface area with sensitivity is somewhat compromised.

Small Volume Adsorption Measurement Test Chamber

A test chamber was constructed to obtain adsorbed amounts for small volumes of porous silicon not readily measured with existing semiconductor microfabrication analytical tools. Heated desorption of adsorbed gas and liquid increases chamber pressure which is monitored by membrane deflection. Calibration of temperature and deflection permits calculation of adsorbed amount. Exposure of porous silicon to adsorbent is currently done first, followed by low temperature bonding of top to bottom die. However, a small check valve could be integrated for multiple exposure uses. Membrane deflection is currently measured using stylus profilometer, but could also be obtained using laser reflectance or capacitive techniques. Thus, microactuators of various types as well as expandable devices can conceivably be constructed.

Figure 2:
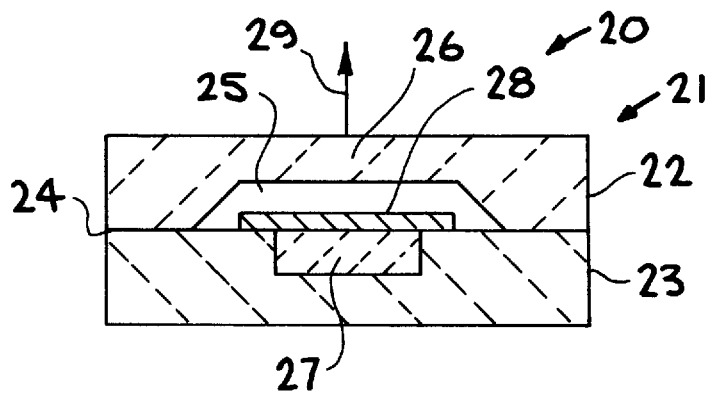
FIG. 2 schematically illustrates an embodiment of a device using a porous silicon membrane as a deflection member.

FIG. 2 schematically illustrates in cross-section an embodiment of adsorption device using porous silicon and having a deflectable membrane. The gas or fluid device generally indicated at 20 comprises a substrate or body 21 composed of two (upper and lower) silicon members 22 and 23 bonded together as indicated at 24. Upper member 22 is provided with a cutaway or chamber 25 defining a thin membrane 26 (thickness of 0.01 μm to 1 cm, preferably about 50 μm). A section of the lower member 23 is etched or otherwise processed, as described hereinafter, to form a porous silicon layer or membrane 27, and a heater 28, composed of a metal such as gold or platinum with a chromium interfacial adherence layer, doped silicon, or doped polysilicon, for example, is positioned in cutaway or chamber 25 over the porous silicon layer or membrane 27. The porous silicon layer 27 is exposed to an adsorbent (gas or fluid) followed by increase in temperature by heater 28 which causes the gas or fluid to desorb from layer 27 and increases the pressure in cutaway or chamber 25 causing outward deflection of membrane 26 as indicated by arrow 29. Reducing the temperature of layer 27 causes readsorption of the gas or fluid causing the membrane 26 to retract.

A detailed example of the process for fabricating the FIG. 2 embodiment is as follows:

Deposit a silicon nitride layer on one side of silicon substrate 23, diffuse backside to form a p++ layer, pattern the silicon nitride layer and form the porous silicon layer 27. Remove the silicon nitride pattern and form heater 28 over a fraction of the area of the porous silicon layer. Form a tapered opening in silicon substrate 22 by micromachining or etching to produce the resultant membrane 26. After exposure of the porous silicon to a desired adsorbent, bond substrate 22 to substrate 23 using a low temperature bond technique such as epoxy applied at interface 24 compatible with negligible desorption of adsorbent. Note that with use of appropriate check valve and adsorbent exposure after bonding, higher temperature bonding techniques not compatible with desorption of adsorbent can then be employed.

Figure 6:
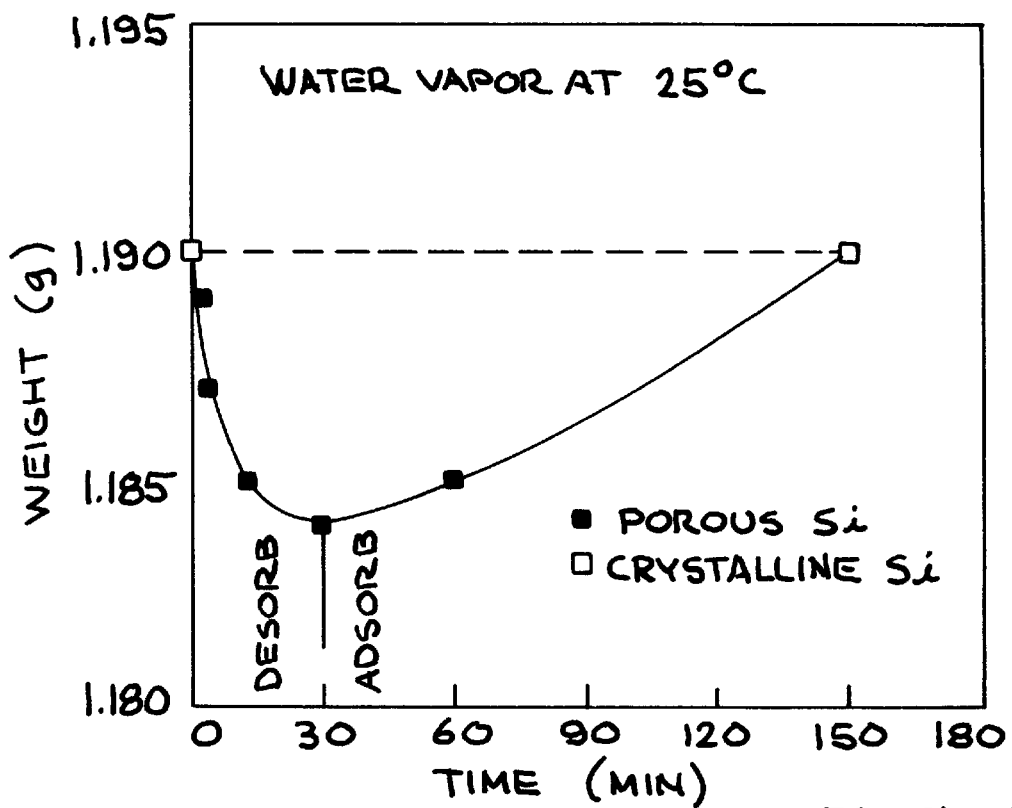
FIG. 6 graphically illustrates the gas absorption-desorption characteristics of crystalline silicon and porous silicon.

Tests have been carried out to determine the adsorption-desorption characteristic of porous silicon with 10 nm pore diameter compared to crystalline silicon using water vapor @25° C., and the results of are shown in FIG. 6. These tests also provided the following for porous silicon:

1. Adsorption Flux (mg/sq cm-hr)
   0.3 for water
   0.9 for ethanol
2. Desorption Flux (mg/sq cm-hr)
   1.1 for water
   1.7 for ethanol
3. Adsorption Capacity
   32 mg/cc for water
   150 mg/cc for ethanol Controlled Flow Gas/Fluid Interface Incorporation of a porous silicon membrane interface between two analytical devices, such as a reaction chamber and an analytical channel, for example, is another application. By placing heaters within or adjacent to the membrane the interconnection could be controlled allowing programmable flow between the two devices. Electrodes within or adjacent the porous membrane could be used similarly to control flow of electrically charged bio/chemical species such as in electrophoresis/electrokinetic injection.

Figure 3:
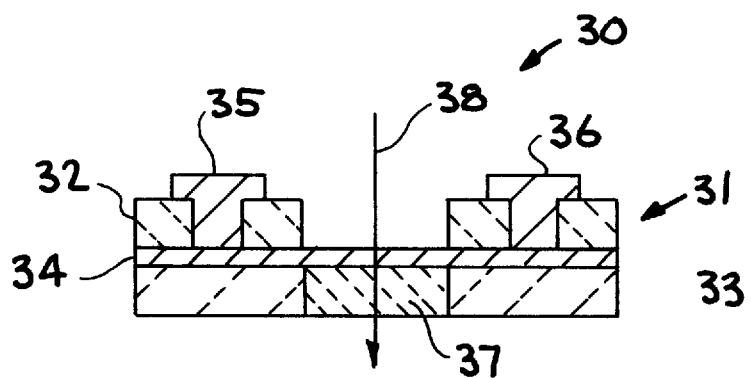
FIG. 3 schematically illustrates an embodiment of a device using a porous silicon membrane as a gas or fluid flow controller.

FIG. 3 schematically illustrates in cross-section an embodiment of a controlled flow interface device. As shown the device, generally indicated at 30 comprises a substrate or body 31 composed of an upper Pyrex member 32 and lower member silicon 33 having a heater 34 positioned therebetween and bonded to members 32 and 33. Electrodes 35 and 36 are located or formed in upper member 32 and a section of lower member 33 is etched or processed to for a porous silicon membrane 37. Heating of the membrane 37 enables control of gas or fluid flow through the membrane 37 as indicated by arrow 38. The membrane 37 may be coated with selected materials. While not shown, the heater 34 could be constructed such that the gas or fluid flow would not pass there through or could be constructed with sufficient porosity to allow for unrestricted gas or fluid flow, or provide fluid viscosity control. The electrodes 35 and 36 are connected to a power source, not shown, for controlling current flow therebetween such as via heater 34.

A detailed example of the process for forming the FIG. 3 embodiment is as follows:

First, the backside of a silicon wafer is diffused to form a heater resistor 34. Silicon nitride is then deposited on the polished side of the wafer in a local region at the desired position for the porous silicon membrane. The, Pyrex member 32 with drilled holes is anodically bonded to the silicon wafer with one hole placed within the local nitride area and two other adjacent holes for electrode contact to the heater. Etchback of the silicon to 5 μm thickness is performed to form silicon member 33. Electrodes 35 and 36 are deposited through a shadow mask to contact the heater 34, followed by porous silicon formation and removal of the local nitride to form the membrane 37.

PCR/Electrophoresis Interface

A DNA integration application requires an interface element between the PCR, or chemical reaction chamber, and electrophoresis devices that can control the flow of fluid after reaction cycling and deliver nanoliter quantity. The interface element described hereinafter with respect to FIGS. 4 and 5 utilizes a porous silicon membrane with an adjacent heater. The heater is used to control the surface tension or viscosity of the fluid in order to control its flow between the PCR and electrophoresis device.

Figure 4:
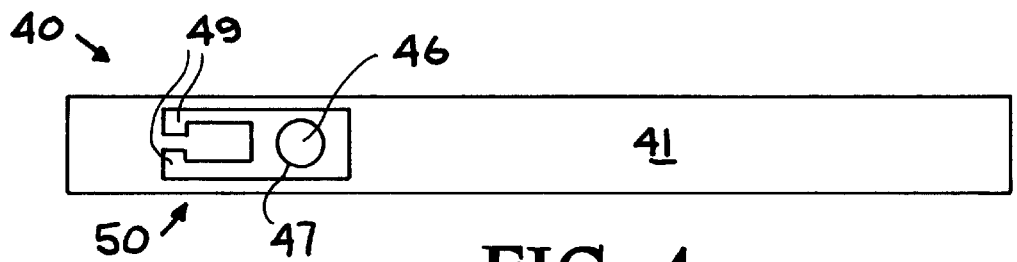
FIG. 4 is a top view of an electrophoresis device using a porous silicon membrane as an interface element with a PCR.
Figure 5:
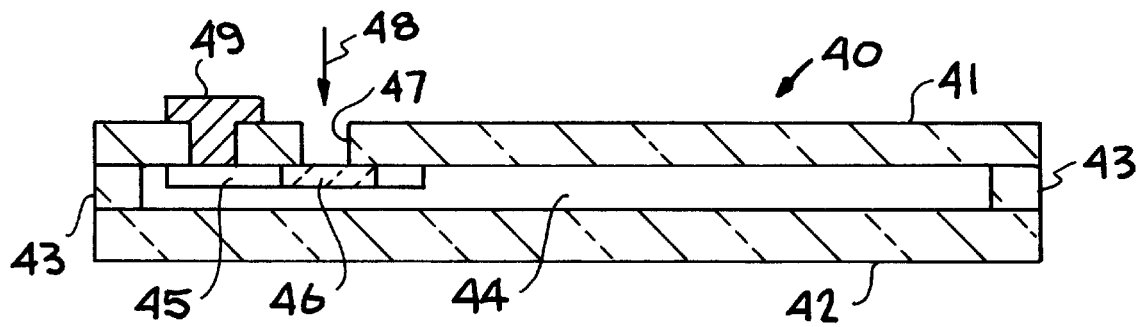
FIG. 5 is a cross-sectional side view of the device of FIG. 4.

An integrated PCR/electrophoresis interface is illustrated in FIGS. 4 and 5. The electrophorus device is typically made by bonding two pieces or plates of Pyrex together for electrical insulation during high voltage separation. The channel depth is also required to be small at about 100 μm. A thinned silicon structure of about 50 μm thickness have a section thereof made porous to form a membrane, to positioned and bonded on the underside of the top Pyrex plate. The thin silicon member containing the porous silicon membrane fits into one end of an electrophoresis channel formed by the two Pyrex plates. Contact between the porous silicon membrane and an adjacent heater is made through offset holes in the top Pyrex plate for fluid flow control. A hole in the to Pyrex plate above the membrane permits DNA input from the PCR reaction chamber.

Referring now to FIGS. 4 and 5 which illustrate an embodiment of a PCR/electrophoresis integrated interface, the device generally indicated at 40, comprises a pair of Pyrex substrates or plates 41 and 42 interconnected by end members 43 to define an electrophoresis channel 44, having a depth of about 100 μm, for example. Channel 44 may be formed by grooves or microchannels in either or both of plates 41 and 42, thereby eliminating end members 43. A silicon member 45 having a section etched or processed to form a porous silicon membrane 46 is bonded to upper Pyrex plate 41. An opening 47 is formed in plate 41 and functions as a PCR input as indicated by arrow 48. A pair of openings 49, only one shown, are formed in plate 41 in which contacts 49 of a heater 50 are deposited. The heater 50 may be deposited on the out surface of Pyrex plate 41 so as to extend around opening 47, as shown in FIG. 4, or it may be deposited in the silicon member 45 or on the inner surface of plate 41.

Various methods to form porous silicon membranes in {100} silicon substrates, with a variety of pore sizes (about 10 nm to about 1 μm) were carried out. One method which utilizes a silicon nitride mask for etch resistance to a 49% (HF) etchant, such as used to form the membrane of FIG. 1, was found to be not acceptable for applications using Pyrex support members (FIGS. 4–5) since its deposition temperature is not compatible with the Pyrex. Porous silicon membrane definition using an O-ring seal mounted in a Teflon holder was used instead. Electrochemical current was not obtained for 1 mm diameter Teflon holes as the HF etch solution did not make adequate contact to the silicon surface. Current was obtained for 2 mm diameter holes by priming the hole with etch solution using a microliter dispenser tool, but bubble formation broke the solution-silicon contact. Removal of the bubbles restored the current. Ultrasonic agitation during formation is being tested to alleviate the bubble formation problem.

Alternative chemical etch techniques were then carried out to form different size pores in the silicon membrane. A low temperature oxide film compatible with the Pyrex was deposited onto thinned {110} silicon as a pattern mask for 42% potassium hydroxide (KOH) chemical etch. Etch tests on polished silicon surfaces indicated a vertical wall porous silicon material was formed. The silicon walls were 3 μm thick separated by 7 μm grooves with an etch depth of about 60 μm over a 6 mm diameter area. However, resist definition on the thinned silicon obtained using wet chemical etchback gave excessively variable line width. This effect was presumed due to the relatively large surface roughness of the thinned silicon at about 10 μm peak-to-peak. Experiments using grindback techniques capable of less than 0.1 μm roughness are being carried out as well as attempts to improve the wet chemical etchback to overcome this problem.

The fluid transport characteristic of porous silicon is important for the DNA integration interface element application (FIGS. 4–5). A test set-up is being devised to permit filling of a flow line with liquid on one side of a porous silicon membrane followed by pressurization. Heating of the membrane can be done by exposure to a hot air gun or use of an above-described integral heater element adjacent to the porous silicon membrane.

Figure 7A:
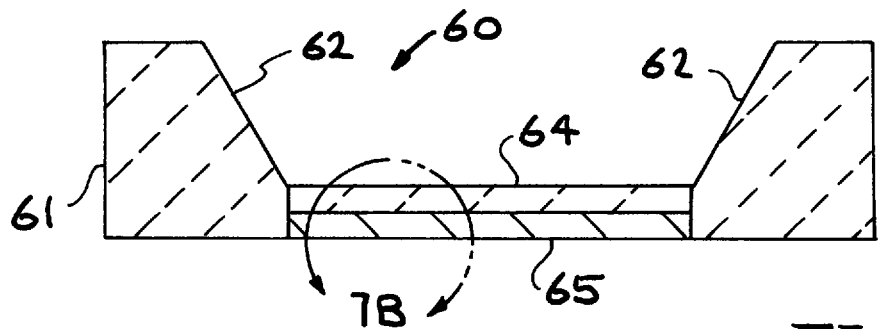
FIGS. 7A and 7B illustrate a micro/nanoporous silicon heated reaction chamber.
Figure 7B:
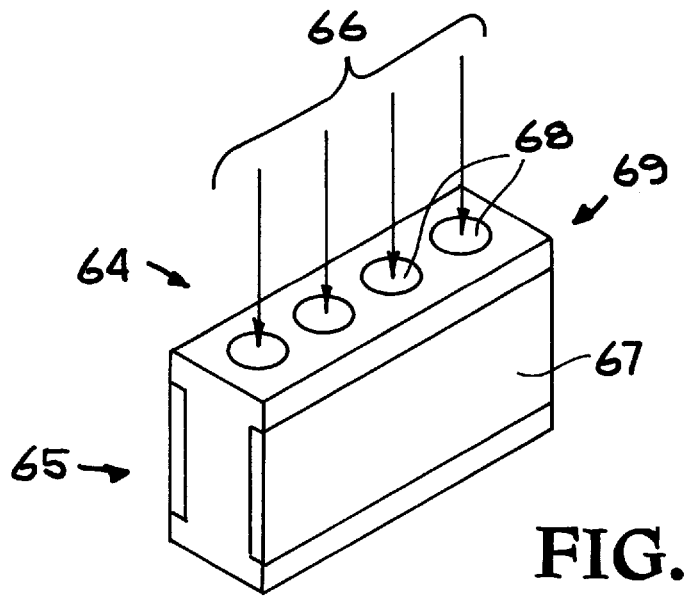

FIGS. 7A and 7B illustrate an embodiment of a micro or nanopore chemical reactor made in accordance with the present invention, with FIG. 7B being an enlarged section of FIG. 7A indicated by the circle and arrow in FIG. 7A. As shown in FIG. 7A the reactor generally indicated at 60 is composed of a silicon substrate 61 having a tapered section 62 forming a bridge or thinned section 63' in silicon substrate 61, with a porous silicon section 64 defining a reactor structure, and an integrated heater section 65; porous section 64 and heater section 65 being formed in the bridge or thinned section 63 of silicon substrate 61, as described above. As seen in FIG. 7B the porous section 64 and heater section 65 are constructed to form a plurality of pore-reactors 66 with an integrated heater 67 extending there across. The pore-reactors 66 are formed, for example, by electrochemical etching of spaced regions along the bridge or thinned section 63 of silicon substrate 61 to form a plurality of spaced porous silicon members or columns 68 which may extend partially or entirely through the bridge or thinned section 63. Thus, the pore-reactors 66 and integrated heater 67 form a micro/nanoheated reaction chamber, generally indicated at 69. As described above the individual micro/nanoreaction chambers or porous silicon columns 68 may have a pore size from about 1 μm to about 10 nm.

Figure 8:
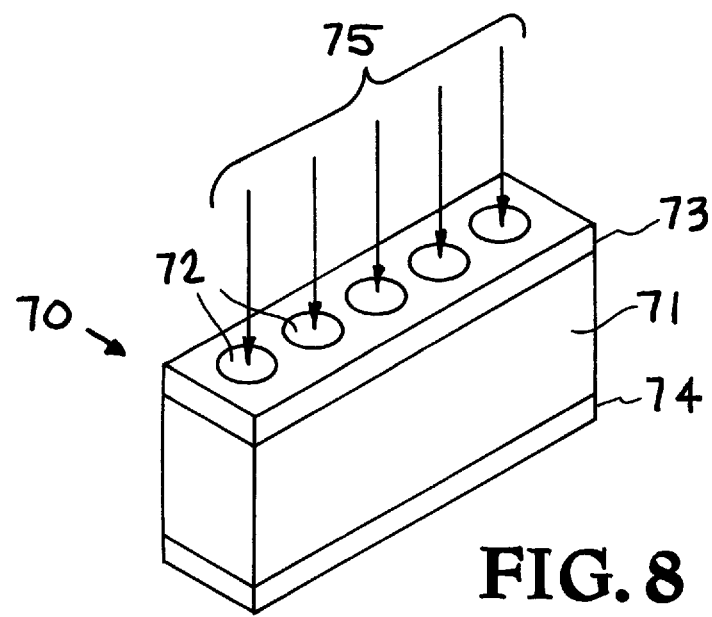
FIG. 8 illustrates a micro/nanoporous silicon electrophoresis device.

FIG. 8 illustrates an embodiment of a porous silicon electrophoresis device made in accordance with the present invention. The electrophoresis device generally indicated at 70 comprises a silicon member 71 in which a plurality of spaced members or columns 72 of porous silicon are formed, as described. above. A negative electrode 73 is formed at one (inlet) end of porous silicon members or columns 72 and a positive electrode 74 is formed at an opposite (outlet) end of porous silicon members or columns 72, as described above, thereby forming micro/nanoelectrophoresis channels generally indicated at 75, with the porous silicon of members or columns 72 having a pore size of about 1 μm down to about 10 nm.

Initial development and testing of various porous silicon films using electrochemical and chemical etching technology wherein basic properties of the films, as well as the adsorption/desorption and gas transport characteristics, have been measured. Also, fabrication procedures for porous silicon membrane structures on silicon and Pyrex have been developed.

It has thus been shown, that micromachined devices using porous silicon membranes have many applications, such as micro-valves for fluid/gas transport, fluid viscosity control, actuators (one shot or repeated movement) using desorption/adsorption of coated materials, interface elements between analysis apparatus, etc. Thus, by the use of porous silicon membranes, chemical reaction systems, electrophoresis devices, preconcentrator structures for analytical instruments, thermopneumatic or thermofluidic valves, filters for biological/chemical sample preparation, etc. can be more effectively utilized. Thus, the use of porous silicon members has potential for greatly advancing these fields of technology.

While particular embodiments, fabrication process, materials, parameters, etc., have been illustrated or described to exemplify and explain the principles of the invention, such are not intended to be limiting. Modification and changes may become apparent to those skilled in the art, and it is intended that the invention be limited only by the scope of the appended claims.

We claim:

1. In a device through which fluid or gas is adapted to pass, the improvement comprising:
   at least one porous silicon member having pores in the range of less than about 1 μm,
   said porous silicon member defining a section of a crystalline silicon member.

2. The improvement of claim 1, wherein said porous silicon member pores are in the range of about 10 nm to about 1 μm.

3. The improvement of claim 1, wherein said porous silicon member has a thickness of about 50 μm.

4. The improvement of claim 1, additionally including a coating of material on said porous silicon member.

5. The improvement of claim 4, wherein said coating is composed of material which undergoes desorption-upon heating and adsorption upon cooling.

6. The improvement of claim 5, additionally including means for heating and cooling the porous silicon member.

7. The improvement of claim 1, wherein said porous silicon member contains absorbed amounts of gas or fluid.

8. The improvement of claim 1, additionally including means for heating said porous silicon member.

9. The improvement of claim 1, wherein said porous silicon member is positioned in a chamber and contains a desorbable material, and additionally including means for heating said porous silicon member causing desorption of said material creating an increase in pressure in said chamber.

10. The improvement of claim 9, wherein said chamber is constructed to include a thin section, and increase in pressure in said chamber causes deflection of said thin section.

11. The improvement of claim 1, wherein said porous silicon member defines an interface between two-analysis devices, and additionally including means for heating said porous silicon member for controlling flow between said two analysis devices.

12. The improvement of claim 11, wherein said two analysis devices comprise a PCR and an electrophoresis device.

13. The improvement of claim 12, wherein at least one of said analysis devices includes a plurality of spaced porous silicon members.

14. The improvement of claim 13, wherein the plurality of spaced porous silicon members is provided with a heater means or positive/negative electrode means.

15. The improvement of claim 11, wherein said porous silicon member is located in one of said analysis devices which is constructed of two plates bonded together and constructed to form at least one electrophoresis channel therein.

16. The improvement of claim 1, wherein said porous silicon member is formed by processing a section of the crystalline silicon member to produce pores therein in a range of about 5 nm to about 100 nm.

17. The improvement of claim 1, wherein said porous silicon member defines at least one wall surface of a chemical reactor thereby providing a greater surface area in said chemical reactor.

18. The improvement of claim 1, wherein said porous silicon member is located in a crystalline silicon member and provided with thin film electrodes to produce electromotive force through pores of said porous silicon which are utilized as electrophoresis channels.

19. A porous silicon member defining a section of a crystalline silicon member and having pores in the range of about 1–10 nm to about 1 µm.

20. The porous silicon member of claim 19, constructed by processing said section of said crystalline silicon member.

21. The porous silicon member of claim 19, wherein said pores contain adsorbed or coated materials, said porous silicon member being provided with heating means.

22. The porous silicon member of claim 19, additionally including a heater means therefore, whereupon change in temperature changes flow of a material through said porous silicon member.

23. The porous silicon member of claim 19, in combination with devices selected from the group consisting of a microfabricated chemical reactor, a micro-valve, a micro chemical preconcentrator, a dual analysis system, an actuator, and filter system, and an electrophoresis system.

* * * * *